United States Patent [19]

Phillips et al.

[11] Patent Number: 4,589,992
[45] Date of Patent: May 20, 1986

[54] NEW SALTS USEFUL AS CORROSION INHIBITORS

[75] Inventors: Emyr Phillips, Sale; David Wilson, Tyldesley, both of England

[73] Assignee: Ciba-Geigy Corporation, Ardsley, N.Y.

[21] Appl. No.: 661,624

[22] Filed: Oct. 17, 1984

[30] Foreign Application Priority Data

Oct. 19, 1983 [GB] United Kingdom ............... 8327911

[51] Int. Cl.$^4$ ............... C10M 129/40; C10M 133/08
[52] U.S. Cl. ............................. 252/75; 252/34; 252/76; 252/78.1; 252/79; 252/387; 252/388; 252/389.1; 252/389 R; 260/501.17; 560/1; 560/105; 560/222; 560/225
[58] Field of Search .............. 252/34, 75, 76, 78.1, 252/79, 387, 388, 389.1; 260/501.17; 560/1, 105, 222, 225

[56] References Cited

U.S. PATENT DOCUMENTS

| | | | |
|---|---|---|---|
| 2,962,443 | 11/1960 | Rhodes | 252/56 |
| 3,392,116 | 7/1968 | Hornus | 252/34 |
| 3,720,615 | 3/1973 | Izumi et al. | 252/33 |
| 3,775,320 | 11/1973 | Vigo et al. | 252/34 |
| 3,981,682 | 9/1976 | Ward et al. | 21/2.7 R |
| 4,040,798 | 8/1977 | Kuhn et al. | 252/34 |
| 4,071,327 | 1/1978 | Dorer, Jr. | 260/501.17 |
| 4,072,626 | 2/1978 | Finney | 252/388 |
| 4,179,522 | 12/1979 | Huitson | 424/317 |
| 4,294,714 | 10/1981 | Lewis et al. | 252/34 |

FOREIGN PATENT DOCUMENTS 1544935 4/1979 United Kingdom.

Primary Examiner—Paul Lieberman
Assistant Examiner—Robert A. Wax
Attorney, Agent, or Firm—Luther A. R. Hall

[57] ABSTRACT

Salts having the formula:

$$Y-NH_3^+ \cdot RCO_2^- \qquad \qquad I$$

in which Y is a group of formula $R^1XCH_2CH(OH)CH_2-$, R and $R^1$ are the same or different and each is a straight- or branched chain alkyl group having from 1 to 18 carbon atoms, a straight- or branched chain alkenyl group having from 2 to 18 atoms, a cycloalkyl group having from 4 to 12 ring atoms, an aryl group having 6-10 ring atoms, or an aralkyl group having from 7 to 10 carbon atoms; and X is O, $CO_2$, $NR^2$ or S and $R^2$ is hydrogen, a straight- or branched chain alkyl group having from 1 to 18 carbon atoms or an alkenyl group having from 2 to 18 C atoms.

8 Claims, No Drawings

NEW SALTS USEFUL AS CORROSION INHIBITORS

The present invention relates to new salts; to processes for their production; and to their use as corrosion inhibitors for metals in non-aqueous fluids.

Water can be present, as a contaminant, in the systems containing such fluids. As a consequence of the presence of this water, corrosion of metals, especially ferrous metals, in contact with such systems, is a serious and costly problem.

A particular aspect of this problem is the rusting of ferrous metals in internal combustion engines, steam turbines, hydraulic systems, oil pipelines, storage vessels and the corrosion caused during machining operations.

Previous attempts to overcome this problem have involved the use, as corrosion inhibitors, of (a) the reaction product of a substituted succinic acid and an alkylene oxide (U.S. Pat. No. 2,962,443);

(b) a mixture of (i) a 7–44C polycarboxylic acid having 2 or 3 carboxyl groups, or a partial ester thereof with a 1–18C aliphatic alcohol and (ii) an aliphatic tertiary amine having three hydrocarbon groups, each of which has at least 1–20C atoms and at least one of which has 6–20C atoms, the weight ratio of (i) to (ii) being from 95:5 to 5:95 (U.S. Pat. No. 3,720,615); or (c) a liquid dicarboxylic acid having the formula:

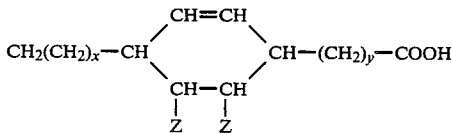

in which x and y are integers from 3 to 9, the sum of x and y being 12, and Z is H or COOH; as well as mono- or bis alkanolamides of said dicarboxylic acid, or a monoalkanolamide derivative of a soap of said dicarboxylic acid (GB No. 1439899).

Moreover, Japanese Patent Publication No. 15783/1973 describes a rust inhibitor consisting of a derivative of a gamma-alkoxypropylamine having the formula:

$$R-O-CH_2CH_2CH_2NH_2$$

in which R is an alkyl group. More particularly, it relates to a method of inhibiting rusting of metals by dissolving a reaction product of a gamma-alkoxypropylamine and a fatty acid in water or oil, at elevated temperature, preferably 120°–140° C.

Surprisingly, we have now found that certain salts, produced from starting materials very similar to those employed in Japanese Patent Publication No. 15783/1973, unexpectedly have superior effectivity as corrosion inhibitors in such media, when compared to the said Japanese inhibitors.

Accordingly, the present invention provides salts having the formula (I):

$$Y-NH_3^{\oplus} \cdot RCO_2^{\ominus} \quad (I)$$

in which Y is a group of formula $R^1XCH_2CH(OH)CH_2-$, R and $R^1$ are the same or different and each is a straight- or branched chain alkyl group having from 1 to 18 carbon atoms, a straight- or branched chain alkenyl group having from 2 to 18 carbon atoms, a cycloalkyl group having from 4 to 12 ring carbon atoms, an aryl group having 6–10 ring carbon atoms or an aralkyl group having from 7 to 11 carbon atoms; and X is O, $CO_2$, $NR^2$ or S and $R^2$ is hydrogen, a straight- or branched chain alkyl group having from 1 to 18 carbon atoms, or an alkenyl group having from 2–18C atoms.

When R and/or $R^1$ and/or $R^2$ is a $C_1$–$C_{18}$ straight- or branched chain alkyl group, they may be e.g. methyl, ethyl, n-propyl, isopropyl, n-butyl, isobutyl, s-butyl, t-butyl, n-pentyl, n-hexyl, n-heptyl, n-octyl, isooctyl, n-nonyl, n-decyl, n-undecyl, n-dodecyl, n-tridecyl, n-tetradecyl, n-pentadecyl, n-hexadecyl, n-heptadecyl or n-octadecyl.

When R and/or $R^1$ and/or $R^2$ is a $C_2$–$C_{18}$ straight- or branched-chain alkenyl group, they may be e.g. vinyl, propenyl, but-3-enyl, pentenyl, hexa-2,4-dienyl, octa-2,6-dienyl, decenyl, deca-1,3-decenyl, oleyl or linoleyl. Such alkyl or alkenyl groups may also be interrupted by one or more heteroatoms e.g. O, S or by an NH group.

When R and/or $R^1$ is a cycloalkyl group they may be e.g. cyclobutyl, cyclopentyl, cyclohexyl, cycloheptyl, cyclooctyl, cyclononyl, cyclodecyl, cycloundecyl or cyclododecyl.

When R and/or $R^1$ is a $C_6$–$C_{10}$ aryl group, they may be e.g. phenyl or naphthyl.

When R and/or $R^1$ is an $C_7$–$C_{11}$ aralkyl group they may be e.g. benzyl, α- or β-phenethyl, α,α-dimethylbenzene or 1- or 2-naphthylmethyl.

When R and/or $R^1$ is a cycloalkyl, aryl or aralkyl group, they may optionally be substituted by one or more 1–4C alkyl groups, hydroxyl groups, amino groups or carboxyl groups.

Preferred salts of formula I are those wherein R is a straight- or branched chain $C_1$–$C_{18}$ alkyl—(more preferably $C_{10}$–$C_{18}$) or 2–18C alkenyl group and Y is a group $R^1XCH_2CH(OH)CH_2-$ in which X is O or $CO_2$ and $R^1$ is straight- or branched chain $C_1$–$C_{18}$ alkyl group.

More preferred are those salts of formula I wherein the total carbon number is between 15 and 39, especially between 23 and 39. Salts having a carbon number within these limits provide excellent corrosion-inhibiting activity combined with good solubility in non-aqueous functional fluids.

The new salts of formula I may be produced by forming a salt preferably by simply mixing an amine having the formula $Y-NH_2$ wherein Y has its previous significance, with an acid of formula $RCO_2H$.

The mixing is conveniently effected at ambient temperature. Any heating applied is preferably to a temperature below 100° C.; preferably from 20°–40° C. and only that required to produce a homogeneous mixture of the amine and acid salt precursors.

The mixing may be effected in an inert solvent if desired e.g. in an aromatic hydrocarbon e.g. toluene.

The weight ratio of amine to acid may be in the range of from 1:3 to 3:1 but a weight ratio of substantially 1:1 is preferred.

Examples of amines of formula $YNH_2$ include the following:

X=O $CH_3OCH_2CH(OH)CH_2NH_2$ $C_2H_5OCH_2CH(OH)CH_2NH_2$ $n-C_3H_7OCH_2CH(OH)CH_2NH_2$ n—$C_4H_9OCH_2CH(OH)CH_2NH_2$ n—$C_5H_{11}OCH_2CH(OH)CH_2NH_2$ n—$C_6H_{13}OCH_2CH(OH)CH_2NH_2$ n—$C_7H_{15}OCH_2CH(OH)CH_2NH_2$ n—$C_8H_{17}OCH_2CH(OH)CH_2NH_2$ n—$C_9H_{19}OCH_2CH(OH)CH_2NH_2$ n—$C_{10}H_{21}OCH_2CH(OH)CH_2NH_2$ n—$C_{12}H_{25}OCH_2CH(OH)CH_2NH_2$ n—$C_{14}H_{29}OCH_2CH(OH)CH_2NH_2$ n—$C_{16}H_{33}OCH_2CH(OH)CH_2NH_2$ n—$C_{18}H_{37}OCH_2CH(OH)CH_2NH_2$ n—$C_{18}H_{35}OCH_2CH(OH)CH_2NH_2$ cyclo—$C_6H_{11}OCH_2CO(OH)CH_2NH_2$ cyclo—$C_8H_{15}OCH_2CH(OH)CH_2NH_2$ cyclo—$C_{12}H_{23}OCH_2CH(OH)CH_2NH_2$ $C_6H_5OCH_2CH(OH)CH_2NH_2$ Products from isopropylated phenols as e.g.

2—i—$C_3H_7$—$C_6H_4OCH_2CH(OH)CH_2NH_2$

4—i—$C_3H_7$—$C_6H_4OCH_2CH(OH)CH_2NH_2$ 2,6—Di—i—$C_3H_7$—$C_6H_3OCH_2CH(OH)CH_2NH_2$ 3,5—Di—i—$C_3H_7$—$C_6H_3OCH_2CH(OH)CH_2NH_2$ $C_{10}H_7OCH_2CH(OH)CH_2NH_2$ $C_6H_5CH_2OCH_2CH(OH)CH_2NH_2$ $C_{10}H_7CH_2OCH_2CH(OH)CH_2NH_2$ $X = CO_2$ $CH_3CO_2CH_2CH(OH)CH_2NH_2$ $C_2H_5CO_2CH_2CH(OH)CH_2NH_2$ $C_9H_{19}CO_2CH_2CH(OH)CH_2NH_2$ n—$C_{18}H_{37}CO_2CH_2CH(OH)CH_2NH_2$ $X = NR^2$ $(C_2H_5)_2NCH_2CH(OH)CH_2NH_2$ $(CH_3)_2NCH_2CH(OH)CH_2NH_2$ $(C_6H_{13})_2NCH_2CH(OH)CH_2NH_2$ $(C_9H_{19})_2NCH_2CH(OH)CH_2NH_2$ $X = S$ $CH_3SCH_2CH(OH)CH_2NH_2$ $C_2H_5SCH_2CH(OH)CH_2NH_2$ $C_{12}H_{25}SCH_2CH(OH)CH_2NH_2$ $C_{18}H_{37}SCH_2CH(OH)CH_2NH_2$

Examples of acids of formula $RCO_2H$ include the following: acetic acid, propionic acid, butyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid or octadecanoic acid; acrylic acid, methacrylic acid, propenoic acid, butenoic acid, hexenoic acid, heptenoic acid, octenoic acid, nonenoic acid, decenoic acid, undecenoic acid, dodecenoic acid, tetradecenoic acid, hexadecenoic acid or octadecenoic acid; cyclohexane carboxylic acid, cyclooctane carboxylic acid, benzoic acid or α- or β-naphthoic acid, phenylacetic acid, phenylpropionic acid or α,α-dimethylphenylacetic acid, or naphthylacetic acid.

The amines of formula $Y-NH_2$ and the acids of formula $R-CO_2H$ are mostly known compounds and many are commercially-available. Any new amines or acids within these classes can be prepared by methods well-known to the art-skilled. For example, the hydroxyamine starting materials may be produced by treating, with dilute aqueous ammonia, an epoxy compound of formula:

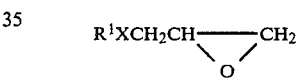

wherein $R^1$ and X have their previous significance.

The new salts of formula I are excellent corrosion inhibitors for metals, especially ferrous metals, in contact with non-aqueous fluids contaminated with water.

Accordingly, the present invention further provides a composition comprising a major proportion of a non-aqueous functional fluid and, as corrosion inhibitor, a corrosion-inhibiting proportion preferably from 0.001 to 5% by weight of a salt of formula I as hereinbefore defined.

The non-aqueous functional fluid may be a lubricating oil e.g. a natural or synthetic lubricating oil; a refined petroleum product such as a fuel oil, diesel oil, kerosene, gasoline or aviation fuel; or a hydraulic fluid e.g. a phosphate-based synthetic oil.

The lubricating oil may be a mineral oil, a synthetic oil or any mixture of such oils. Mineral oils are preferred and examples of these include paraffinic hydrocarbon oils e.g. a mineral oil having a viscosity of 46 $mm^2/s$ at 40° C.; "150 Solvent Neutral" a solvent refined neutral mineral having a viscosity of 32 $mm^2/s$ at 40° C.; and "Solvent brightstocks", a high-boiling residue from the process of refining mineral oil, and having a viscosity of 46 $mm^2/s$ at 40° C.

Synthetic lubricating oils which may be present may be synthetic hydrocarbons such as polybutenes, alkyl benzenes and poly-alpha olefins as well as simple di-, tri- and tetraesters, complex esters and polyesters derived from carboxylic acids and hydroxy compounds. Preferred are dicarboxylic acid esters of formula:

$$R^3\text{—OOC—alkylene—COOR}^4$$

wherein "alkylene" denotes an alkylene residue having from 2 to 14 carbon atoms and $R^3$ and $R^4$ are the same or different and each is an alkyl group having from 6 to 18 carbon atoms.

Tri-esters which are of use as lubricating oil basestocks are those derived from trimethylolpropane and C6–C18 monocarboxylic acids or mixtures thereof, whereas suitable tetraesters include those derived from pentaerythritol and a C6–C18 monocarboxylic acid or mixtures thereof.

Complex esters suitable for use as components of the compositions of the present invention are those derived from monobasic acids, dibasic acids and polyhydric alcohols, for instance the complex ester derived from trimethylol propane, caprylic acid and sebacic acid.

Suitable polyesters are those derived from an aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

If desired the salts of formula I may be used in combination with one or more additives conventionally employed in non-aqueous functional fluids, e.g. antioxidants, metal deactivators, further rust inhibitors, viscosity index improvers, pour point depressors, dispersants/surfactants and wear resisting additives.

Examples of antioxidants are:

(a) Alkylated and non-alkylated aromatic amines and mixtures thereof, for example, dioctyldiphenylamine, 2,2,3,3-tetramethylbutylphenyl-α- and -β-naphthylamines, phenothiazine, dioctylphenothiazine, phenyl-α-naphthylamine, N,N'-di-sec-butyl-p-phenylenediamine.

(b) Sterically hindered phenols, for example: 2,6-di-tert-butyl-p-cresol, 4,4'-bis-(2,6-diisopropylphenol), 2,4,6-triert-butylphenol, 4,4'-methylene-bis-(2,6-di-tert-butylphenol).

(c) Alkyl-, aryl- or alkarylphosphites, for example: trinonylphosphite, triphenylphosphite, diphenyldecylphosphite.

(d) Esters of thiodipropionic acid or thiodiacetic acid, for example: dilaurylthiodipropionate or dioctylthiodiacetate.

(e) Salts of carbamic and dithiophosphoric acids, for example: antimony diamyldithiocarbamate, zinc diamyldithiophosphate.

(f) A combination of two or more of the above antioxidants, for example: an alkylated amine and a sterically hindered phenol.

Examples of metal deactivators are:

(a) for copper, e.g. benzotriazole, tolutriazole, tetrahydrobenzotriazole, 2-mercaptobenzothiazole, 2,5-dimercaptothiadiazole, salicylidene propylenediamine, salts of salicylaminoguanidine.

(b) for lead, e.g.: sebacic acid derivatives, quinizarine, propyl gallate.

(c) A combination of two or more of the above additives.

Examples of further rust inhibitors are:

(a) Organic acids, the esters, metal salts and anhydrides thereof, e.g. sorbitan monooleate, lead naphthenate, dodecenylsuccinic-anhydride.

(b) Nitrogen-containing compounds, for example:

I. Primary, secondary or tertiary aliphatic or cycloaliphatic amines and amine salts of organic inorganic acids, for example oil-soluble alkylammonium carboxylates.

II. Heterocyclic compounds, e.g. substituted imidazolines and oxazolines.

(c) Phosphorus-containing compounds, for example: amine salts of phosphoric acid partial esters.

(d) Sulfur-containing compounds, for example, barium dinonylnaphthalenesulfonates, calcium petroleum sulfonates.

(e) Combinations of two or more of the above additives.

Examples of viscosity index improvers are: polymethylacrylates, vinyl pyrrolidone/methacrylate copolymers, polybutene, olefin copolymers, styrene/acrylate copolymers.

Examples of pour-point depressors are: polymethacrylates, alkylated naphthalene derivatives.

Examples of dispersants/surfactants are: polybutenylsuccinimides, polybutenylphosphonic acid derivatives, basic magnesium, calcium and barium sulfonates, phenolates and naphthenates. Dispersants are employed e.g. in concentrations of 0.1 to 1% by weight, based on the lubricant.

Examples of antiwear additives are:

Compounds containing sulfur and/or phosphorus and/or halogen, e.g. sulfurised vegetable oils, and also monothiophosphates, dialkyldithiophosphates or their zinc salts, tritolylphosphates, chlorinated paraffins, alkyl and aryl disulfides.

The following Examples further illustrate the present invention.

EXAMPLE 1

A salt was produced by mixing 20 grams of dodecanoic acid and 20.3 grams of 2-hydroxy-3-isoctyloxy propylamine at ambient temperature. A slight exotherm was observed (final temperature 40° C.). The product, a pale to golden yellow oil, showed the IR spectrum characteristic of an amine salt ($-N^+H_3$ broad centered at 3000 cm$^{-1}$, $-CO_2^-$ strong absorption at 1542 cm$^{-1}$)., having the following elemental analysis by weight:

Found: C 68.02; H 12.58; N 3.02%. Calculated for $C_{22}H_{49}NO_4$: C 67.52; H 12.53; N 3.58%.

EXAMPLES 2 TO 25

In a similar manner, salts were formed from the amines and acids set out in the following Table I:

TABLE I

| Example | Amine of formula YNH$_2$ | Acid of formula RCO$_2$H |
|---|---|---|
| 2 | C$_4$H$_9$CHCH$_2$OCH$_2$CHCH$_2$NH$_2$<br>    \|                  \|<br>   C$_2$H$_5$        OH | C$_{11}$H$_{23}$CO$_2$H |
| 3 | C$_6$H$_{13}$OCH$_2$CHCH$_2$NH$_2$<br>                \|<br>               OH | C$_{11}$H$_{23}$CO$_2$H |
| 4 | C$_4$H$_9$OCH$_2$CHCH$_2$NH$_2$<br>              \|<br>              OH | C$_{11}$H$_{23}$CO$_2$H |
| 5 | C$_3$H$_7$OCH$_2$CHCH$_2$NH$_2$<br>              \|<br>              OH | C$_{11}$H$_{23}$CO$_2$H |

TABLE I-continued

| Example | Amine of formula YNH$_2$ | Acid of formula RCO$_2$H |
|---|---|---|
| 6 | C$_9$H$_{19}$CO$_2$CH$_2$CH(OH)CH$_2$NH$_2$ | C$_{11}$H$_{23}$CO$_2$H |
| 7 | C$_9$H$_{19}$CO$_2$CH$_2$CH(OH)CH$_2$NH$_2$ | C$_{17}$H$_{33}$CO$_2$H |
| 8 | C$_6$H$_{13}$OCH$_2$CH(OH)CH$_2$NH$_2$ | C$_{17}$H$_{33}$CO$_2$H |
| 9 | C$_9$H$_{19}$CO$_2$CH$_2$CH(OH)CH$_2$NH$_2$ | C$_{17}$H$_{35}$CO$_2$H |
| 10 | iC$_8$H$_{17}$OCH$_2$CH(OH)CH$_2$NH$_2$ | CH$_3$(CH$_2$)$_6$CH=CHCO$_2$H |
| 11 | C$_9$H$_{19}$CO$_2$CH$_2$CH(OH)CH$_2$NH$_2$ | CH$_3$(CH$_2$)$_6$CH=CHCO$_2$H |
| 12 | i-C$_{12}$H$_{25}$SCH$_2$CH(OH)CH$_2$NH$_2$ | C$_{17}$H$_{33}$CO$_2$H |
| 13 | C$_6$H$_{13}$OCH$_2$CH(OH)CH$_2$NH$_2$ | C$_{17}$H$_{35}$CO$_2$H |
| 14 | t-C$_{12}$H$_{25}$SCH$_2$CH(OH)CH$_2$NH$_2$ | C$_{11}$H$_{23}$CO$_2$H |
| 15 | cyclo-C$_6$H$_{11}$OCH$_2$CH(OH)CH$_2$NH$_2$ | C$_{11}$H$_{23}$CO$_2$H |
| 16 | cyclo-C$_6$H$_{11}$OCH$_2$CH(OH)CH$_2$NH$_2$ | C$_{17}$H$_{33}$CO$_2$H |
| 17 | PhOCH$_2$CH(OH)CH$_2$NH$_2$ | C$_{17}$H$_{33}$CO$_2$H |
| 18 | PhSCH$_2$CH(OH)CH$_2$NH$_2$ | C$_{17}$H$_{33}$CO$_2$H |
| 19 | C$_9$H$_{19}$CO$_2$CH$_2$CH(OH)CH$_2$NH$_2$ | C$_9$H$_{19}$-C$_6$H$_4$-OCH$_2$CO$_2$H |
| 20 | PhOCH$_2$CH(OH)CH$_2$NH$_2$ | C$_{11}$H$_{23}$CO$_2$H |
| 21 | C$_9$H$_{19}$CO$_2$CH$_2$CH(OH)CH$_2$NH$_2$ | C$_{11}$H$_{23}$CON(CH$_2$CO$_2$H)$_2$ |
| 22 | C$_9$H$_{19}$CO$_2$CH$_2$CH(OH)CH$_2$NH$_2$ | t-C$_9$H$_{19}$CO$_2$H |
| 23 | C$_9$H$_{19}$CO$_2$CH$_2$CH(OH)CH$_2$NH$_2$ | iC$_{17}$H$_{25}$CO$_2$H |
| 24 | iC$_8$H$_{17}$OCH$_2$CH(OH)CH$_2$NH$_2$ | [(CH$_2$)$_4$CO$_2$H]$_2$ |
| 25 | [C$_4$H$_9$CH(C$_2$H$_5$)CH$_2$]$_2$NCH$_2$CH(OH)CH$_2$NH$_2$ | C$_{11}$H$_{23}$CO$_2$H |

In the above Examples, the I.R. spectra of the salts were consistent with the structures proposed.

EXAMPLE 26

Several products of Examples 1-25 were tested as rust inhibitors in a turbine grade mineral oil of viscosity 26 mm$^2$/s at 40° C., 4.8 mm$^2$/s at 100° C. and a typical sulphur content of 0.6% using the ASTM D665A (deionised water) and B (synthetic sea water) methods. The test duration was 24 hours. The results are set out in the following Table II and are expressed as the concentration (in ppm) of the product which will prevent any trace of rusting of the test spindle.

In both A and B tests, absence of additive caused severe-rusting of the test spindle to occur.

TABLE II

| Example No. | Solubility at 20° C. weight % | Minimum concentration (ppm) for zero rusting | |
|---|---|---|---|
| | | A test | B test |
| 1 | >10 | <62 | 125-250 |
| 2 | >10 | <125 | 125-250 |
| 3 | <1 | | <125 |
| 4 | <1 | | 125-250 |
| 5 | <1 | | 125-250 |
| 8 | <1 | | <125 |
| 9 | >10 | | >250 |
| 12 | >1 | <125 | >500 |
| 13 | >10 | | 250 |
| 14 | >1 | 125 | 500 |
| 15 | <1 | | 500 |
| 16 | >1 | 125 | 500 |
| 17 | <1 | | 500 |
| 18 | <1 | | 500 |
| 19 | >1 | | 500 |

What we claim is:

1. A composition having corrosion-inhibition properties which comprises
   (a) a major proportion of a non-aqueous functional fluid; and
   (b) an effective amount of a corrosion inhibitor of a salt of formula I $$Y-NH_3^+ RCO_2^- \qquad (I)$$

in which Y is a group of formula R$^1$XCH$_2$CH(OH)CH$_2$—, R and R$^1$ are the same or different, R$^1$ is a straight- or branched chain alkyl group having from 1 to 18 carbon atoms, a straight- or branched chain alkenyl group having from 2 to 18 carbon atoms, a cycloalkyl group having from 4 to 12 ring carbon atoms, an aryl group having 6–10 ring carbon atoms, or an aralkyl group having from 7 to 10 carbon atoms; R is a straight- or branched chain alkyl group having from 7 to 18 carbon atoms, a straight- or branched chain alkenyl group having from 2 to 18 carbon atoms, a cycloalkyl group having from 4 to 12 ring carbon atoms, an aryl group having 6–10 ring carbon atoms, or an aralkyl group having from 7 to 10 carbon atoms; and X is O, CO$_2$, NR$^2$ or R$^2$ is hydrogen, a straight- or branched chain alkyl group having from 1 to 18 carbon atoms or an alkenyl group having from 2 to 18 carbon atoms.

2. A composition according to claim 1 where in the salt of formula I wherein R is a straight- or branched chain C$_7$-C$_{18}$ alkyl- or C$_2$-C$_{18}$ alkenyl group and Y is a group of formula R$^1$XCH$_2$CH(OH)CH$_2$— wherein X is O or CO$_2$ and R$^1$ is straight- or branched chain C$_1$-C$_{18}$ alkyl group.

3. A composition according to claim 1 wherein the total number of carbon atoms in the salt of formula I is between 15 and 39.

4. A composition according to claim 1 wherein the total number of carbon atoms in the salt of formula I is between 23 and 39.

5. A composition according to claim 1 wherein the non-aqueous functional fluid is a lubricating oil, a refined petroleum product or a hydraulic fluid.

6. A composition according to claim 1 wherein the proportion of the salt of formula I is from 0.001 to 5% by weight, based on the weight of the functional fluid.

7. A composition according to claim 5 wherein the lubricating oil is a natural or synthetic lubricating oil.

8. A composition according to claim 5 wherein the refined petroleum product is a fuel oil, diesel oil, kerosene, gasoline or aviation fuel.

* * * * *